(12) United States Patent  
Pavia

(10) Patent No.: US 10,468,229 B2  
(45) Date of Patent: Nov. 5, 2019

(54) METHOD OF GENERATING A ZOOM SEQUENCE AND MICROSCOPE SYSTEM CONFIGURED TO PERFORM THE METHOD

(71) Applicant: Carl Zeiss Microscopy GmbH, Jena (DE)

(72) Inventor: Giuseppe Pavia, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 865 days.

(21) Appl. No.: 15/079,403

(22) Filed: Mar. 24, 2016

(65) Prior Publication Data

US 2016/0284507 A1     Sep. 29, 2016

(30) Foreign Application Priority Data

Mar. 27, 2015   (EP) ..................................... 15000918

(51) Int. Cl.
*H01J 37/22*     (2006.01)
*H01J 37/28*     (2006.01)
(Continued)

(52) U.S. Cl.
CPC ............ *H01J 37/22* (2013.01); *G02B 21/006* (2013.01); *G02B 21/0016* (2013.01);
(Continued)

(58) Field of Classification Search
CPC .. H01J 37/22; H01J 37/20; H01J 37/26; H01J 37/28; H01J 37/244; H01J 37/153;
(Continued)

(56) References Cited

U.S. PATENT DOCUMENTS 6,570,156 B1    5/2003  Tsuneta et al.
7,576,325 B2 *  8/2009  Gohara ................. H01J 37/222
                                                    250/306
(Continued)

FOREIGN PATENT DOCUMENTS

EP        2 015 342 A2    1/2009

OTHER PUBLICATIONS

P.W. Trimby, "Orientation mapping of nanostructured materials using transmission Kikuchi diffraction in the scanning electron microscope", Ultramicroscopy, vol. 120, 2012, pp. 16-24.
(Continued)

*Primary Examiner* — Brooke Purinton
(74) *Attorney, Agent, or Firm* — Fish & Richardson P.C.

(57) ABSTRACT

The disclosure provides a method of generating a zoom sequence visualizing a portion of a sample. The method includes changing a zoom parameter representing a magnification of an image of a portion of a sample, and directing a charged particle beam to first locations of the portion based on the zoom parameter using a charged particle beam system. The method also includes detecting intensities representing amounts of particles incident onto a detection area, visualizing a representation of the portion based on the intensities, and directing an electron beam to second locations of the portion based on the zoom parameter using a scanning electron microscope. The method further includes detecting diffraction patterns, and determining crystallographic properties of a crystal structure of the portion based on the diffraction patterns.

18 Claims, 9 Drawing Sheets

(51) Int. Cl.
  *G02B 21/00* (2006.01)
  *G02B 21/02* (2006.01)
  *H01J 37/153* (2006.01)
  *H01J 37/244* (2006.01)
  *H01J 37/20* (2006.01)
  *H01J 37/26* (2006.01)

(52) U.S. Cl.
  CPC .......... G02B 21/025 (2013.01); H01J 37/153 (2013.01); H01J 37/20 (2013.01); H01J 37/244 (2013.01); H01J 37/26 (2013.01); H01J 37/28 (2013.01); *H01J 2237/2445* (2013.01); *H01J 2237/2448* (2013.01); *H01J 2237/2602* (2013.01); *H01J 2237/2806* (2013.01)

(58) Field of Classification Search
  CPC ....... H01J 2237/2602; H01J 2237/2806; H01J 2237/2448; H01J 2237/2445; G02B 21/006; G02B 21/0016; G02B 21/025
  See application file for complete search history.

(56) References Cited

U.S. PATENT DOCUMENTS

2004/0011958 A1* 1/2004 Wright ................. G01N 23/203
 250/307
2009/0014651 A1* 1/2009 Kamimura ............ H01J 37/295
 250/311
2011/0220796 A1* 9/2011 Nicolopoulos .. G01N 23/20058
 250/307
2012/0025073 A1* 2/2012 Kumar ................. G01N 23/203
 250/307
2014/0226003 A1 8/2014 Phaneuf et al.
2015/0214004 A1 7/2015 Pavia

OTHER PUBLICATIONS

R.R. Keller et al., "Transmission EBSD from 10 nm domains in a scanning electron microscope", Journal of Microscopy, vol. 245, Pt. 3, 2012, pp. 245-251.

L. Reimer, "Scanning Electron Microscopy: Physics of Image Formation and Microanalysis", Springer, Chapter 9, 1998, pp. 329-377.

Oxford Instruments, "Improving the spatial resolution of EBSD using transmission Kikuchi diffraction in the SEM", Application Note, 2013, pp. 1-4.

R. Keller et al., "Transmission Kikuchi Diffraction in the Scanning Electron Microscope", Bruker Webinar, 2013, pp. 1-36.

Extended European search report for corresponding EP application No. 15 000 918.1 dated Sep. 16, 2015.

* cited by examiner

METHOD OF GENERATING A ZOOM SEQUENCE AND MICROSCOPE SYSTEM CONFIGURED TO PERFORM THE METHOD

CROSS-REFERENCE TO RELATED APPLICATION

This application claims priority under 35 U.S.C. § 119 to European Application No. 15000918.1, filed Mar. 27, 2015. The contents of this application is hereby incorporated by reference in its entirety.

FIELD

The disclosure relates to a method of generating a zoom sequence visualizing a portion of a sample. Furthermore, the disclosure relates to a microscope system configured to perform the method.

BACKGROUND

Conventional scanning electron microscopes (SEM) are configured to scan an electron beam across a portion of a sample and to detect electrons emerging from the sample upon directing the electron beam to the portion of the sample. An intensity of electrons emerging from the sample is detected by an electron detector and associated with a location to which the electron beam is currently directed. Accordingly, an intensity distribution may be determined using the scanning electron microscope, and an image representation of the portion of the sample may be generated based on the intensity distribution.

Usually, a zoom parameter may be defined by a user of the scanning electron microscope in order to select a magnification by which the portion of the sample is magnified in comparison to its actual size. In the scanning electron microscope, the directing of the electron beam depends on the zoom parameter, in particular the electron beam is deflected in dependence of the zoom parameter so that a distance between locations of incidence of the electron beam onto the sample depends on the zoom parameter. For example, a scanning resolution, i.e. a number of locations of incidence of the electron beam onto the sample per unit length or per unit area, increases with increasing zoom parameter, and likewise the scanning resolution decreases with decreasing zoom parameter.

A spatial resolution of the images obtainable using a SEM depends on the size of the spot formed by the electron beam on the sample, which in turn depends on the wavelength of the electrons of the electron beam and the electron-optical system that produces the electron beam. Furthermore, the spatial resolution is limited by an interaction volume in which the electrons of the electron beam interact with the sample. Both the size of the spot and the interaction volume are both large compared to inter-atomic distances of the atoms constituting the sample, so that the crystallographic structure of the sample cannot be resolved using conventional scanning electron microscopes.

In order to resolve the crystal structure of the sample, transmission electron microscopes (TEM) employing electron beams of electrons having kinetic energies much greater than the kinetic energies of the electrons of the electron beams used in a SEM can be used. However, as the kinetic energies of the electrons used in SEM and TEM usually differ by at least one order of magnitude, SEM and TEM are not combined into a single microscope. Accordingly, in order to determine and to visualize the crystal structure of the sample, the sample is transferred from the SEM used to obtain SEM images to a TEM used to obtain images of the crystal structure of the sample. This transferring of the sample to different microscopes implies a plurality of disadvantages such as deterioration of the sample over time, damage of the sample during the transferring of the sample between the microscopes, etc.

SUMMARY

The disclosure seeks to provide a method and an apparatus configured to perform the method which allow to visualize a portion of a sample at both crystal structure level and sample structure level using a single device.

The disclosure was made and the problems above addressed taking the above considerations into account.

According to a first aspect, an embodiment of a method of generating a zoom sequence visualizing a portion of a sample includes changing a zoom parameter representing a magnification of an image of a portion of a sample; directing a charged particle beam to first locations of the portion of the sample based on the zoom parameter using a charged particle beam system, detecting intensities representing amounts of particles incident onto a detection area during the directing of the charged particle beam to the first locations, visualizing a representation of the portion of the sample in the image based on image data representing the intensities if the zoom parameter is less than a predetermined first threshold value; directing an electron beam to second locations of the portion of the sample based on the zoom parameter using a scanning electron microscope, detecting diffraction patterns generated during the directing of the electron beam to the second locations using the scanning electron microscope, determining crystallographic properties of a crystal structure of the portion of the sample for each of the second locations based on the detected diffraction patterns, generating a representation of the crystal structure of the portion of the sample based on the determined crystallographic properties, and visualizing the representation of the crystal structure in the image if the zoom parameter is greater than a predetermined second threshold value.

In this embodiment, both a representation of the portion of the sample, i.e. the sample at a magnification corresponding to the sample structure level, and a representation of the crystal structure of the portion of the sample, i.e. the sample at a magnification corresponding to the crystal structure level, are visualized in an image of a plurality of images of the zoom sequence when changing the zoom parameter from a value below the predetermined first threshold value to a value greater than the predetermined second threshold value and vice versa. Therefore, the zoom sequence may correspond to a plurality of images visualizing the representation of the portion of the sample and the representation of the crystal structure of the portion of the sample. The predetermined first and second threshold values may amount to values in a range about a maximum spatial resolution of the charged particle beam system and/or the scanning electron microscope corresponding to a magnification of 500.000, for example. Herein, the magnification represents a value by which the representation of the portion of the sample and the representation of the crystal structure of the portion are magnified relative to the actual size of the portion of the sample and the actual crystal structure of the portion of the sample, respectively.

The first and second threshold values may amount to a same value. Alternatively, the first threshold value may be greater than the second threshold value. Therefore, only a representation of the portion of the sample at sample structure level is visualized if the zoom parameter is less than the second threshold value, only a representation of the crystal structure of the portion of the sample at crystal structure level is visualized if the zoom parameter is greater than the first threshold value and both a representation of the portion at sample structure level and a representation of the crystal structure at crystal structure level are visualized if the zoom parameter is less than the first threshold value and greater than the second threshold value. For the latter, the representation of the portion of the sample may be magnified by digital signal processing, for example, by interpolating the intensities detected at the first locations. Alternatively, the representation of the portion of the sample may be visualized based on intensities detected while directing the electron beam to the second locations of the portion of the sample.

If the zoom parameter is less than the predetermined first threshold value, a representation of the portion of the sample at sample structure level is visualized. For this, the charged particle beam is directed to the first locations of the portion of the sample based on the zoom parameter using the charged particle beam system. The charged particle beam system may be the scanning electron microscope used for directing the electron beam to the second locations. Accordingly, the charged particle beam may be the electron beam directed to the second locations. Furthermore, the charged particle beam system may be an ion beam system configured to generate an ion beam, for example a beam of gallium-ions, helium-ions, argon-ions, ions of a noble gas, etc. Alternatively, the charged particle beam system may be an electron beam system configured to generate an electron beam different from the electron beam directed to the second locations.

The first locations are arranged within the portion of the sample and may be distributed arbitrarily or in a regular arrangement. In particular, the charged particle beam is directed to the sample so that the first locations, i.e. the locations of the sample to which the charged particle beam is directed, are arranged at a distance to one another corresponding to a scan resolution. A scan resolution, i.e. a spatial frequency representing a distance between the first locations, may be based on the zoom parameter. For example, the scan resolution may be increased when increasing the zoom parameter. Similarly, the scan resolution may be decreased when decreasing the zoom parameter.

Further, during the directing of the charged particle beam to the first locations, intensities representing amounts of particles incident onto the detection area are detected. These particles emerge from the sample upon irradiation with the charged particle beam. Depending on the configuration of the charged particle beam system, these particles may be backscattered or secondary particles, for example backscattered or secondary ions, backscattered or secondary electrons or photons such as X-rays. These particles are incident onto the detection area of at least one detector of the charged particle beam system.

The detector may be an electron detector, an ion detector or an X-ray detector or the like. For example, an electron detector and an ion detector may be configured as a scintillator-photomultiplier system. The at least one detector may be a spatially resolving detector, in particular a detector spatially resolving in two dimensions, which may be implemented using a CCD sensor (charged-coupled device), for example. When using a spatially resolving detector, the intensities may represent the amounts of particles incident onto the detection area integrated over at least a portion of the detection area.

Each of the detected intensities may be associated with a single one of the first locations so that, for each of the first locations, a single intensity representing the amounts of particles incident onto the detection area during the directing of the charged particle beam to the particular first location is detected. Image data may be generated representing the intensities of the first locations, i.e. associated with the first locations.

Further, a representation of the portion of the sample is visualized in the image based on image data representing the intensities. For example, the representation of the portion of the sample may be an image of the detected intensities, i.e. a spatial distribution of intensity values representing the intensities detected at the first locations. The image may be visualized on a display such as a monitor or the like.

Further, if the zoom parameter is greater than the predetermined second threshold value, the portion of the sample is visualized at crystal structure level. For example, a spatial arrangement of spheres representing atoms may be used to visualize the crystal structure of the portion of the sample, thus providing a representation of the crystal structure of the portion of the sample at crystal structure level. For this, the electron beam is directed to the second locations of the portion of the sample based on the zoom parameter using the scanning electron microscope. The second locations may be arranged arbitrarily or in a regular arrangement. In particular, the electron beam may directed to the sample so that a distance between the second locations depends on the zoom parameter, i.e. the scan resolution depends on the zoom parameter. For example, the scan resolution may be increased when increasing the zoom parameter. Similarly, the scan resolution may be decreased when decreasing the zoom parameter. The second locations may be identical to the first locations and the directing of the charged particle beam to the first locations may correspond to the directing of the electron beam to the second locations, and vice versa.

Further, diffraction patterns generated during the directing of the electron beam to the second locations are detected using the scanning electron microscope. In particular, the diffraction patterns may be detected using the at least one electron detector. The diffraction patterns may be two-dimensional spatial distributions of diffracted electrons. Therefore, the at least one electron detector may be a spatially resolving detector, in particular an electron detector spatially resolving in two dimensions.

The diffraction patterns may be generated by diffracted electrons of the electron beam transmitted through the sample and/or reflected back from the sample. Therefore, the detecting of the diffraction patterns may include detecting intensities of diffracted electrons of the electron beam transmitted through the sample and being incident onto the detection area and/or detecting intensities of diffracted electrons of the electron beam reflected from the sample and being incident onto the detection area.

Herein, transmitted through the sample may imply that the detection area is disposed on a side of the sample opposite to the side of the sample onto which the electron beam is incident. Accordingly, reflected from the sample may imply that the detection area is disposed on the side of the sample onto which the electron beam is incident.

Further, crystallographic properties of a crystal structure of the portion of the sample for each of the second locations are determined based on the detected diffraction patterns.

That is, crystallographic properties are determined for each of the second locations so that crystallographic properties of the crystal structure of the sample at a particular second location may be associated with the particular second location.

The crystallographic properties of each location of the second locations, i.e. associated with each of the second locations, may include a crystal lattice type representing a crystal lattice of the crystal structure at the location and an orientation of the crystal lattice relative to a reference coordinate system. However, the crystallographic properties may also include additional information, in particular the lattice parameters corresponding to the crystal lattice type. According to this embodiment, the crystal lattice type representing the crystal lattice of the crystal structure and the orientation of the crystal lattice may be provided as the crystallographic properties at each location of the second locations.

The crystal structure of the sample may be regarded as the spatial arrangement of atoms of the sample. As the sample is usually much larger than inter-atomic distances, the sample and even the portion of the sample inspected using the method described above may include a plurality of regions having different crystal lattice types and/or different orientations of the crystal lattice represented by the different crystal lattice types. Accordingly, the crystal structure of (the portion of) the sample generally includes a plurality of crystal lattices adjoined to each other. Each of the crystal lattices of the crystal structure may be characterized by a crystal lattice type and the orientation of the crystal lattice relative to a reference coordinate system.

Herein, the crystal lattice type characterizes the crystal structure of the sample at a second location. The crystal lattice type may be, for example, one of the types of the Bravais lattices. The crystal lattice represented by a particular crystal lattice type may be regarded as the spatial arrangement of atoms relative to each other in a two- or three-dimensional space. The orientation of the crystal lattice may be regarded as a set of two angels, e.g. $\theta$ and $\varphi$, representing the angular arrangement of the crystal lattice relative to a reference coordinate system such as a coordinate system of the sample, the scanning electron microscope or the like.

The lattice parameters of a particular crystal lattice may include a plurality of primitive vectors of the crystal lattice represented by the lattice parameters and/or parameters representing the primitive vectors.

Further, a representation of the crystal structure of the portion of the sample is generated based on the determined crystallographic properties. The representation of the crystal structure may be regarded as a spatial arrangement of bodies such as spheres, cubes, circles, squares or the like representing the spatial arrangement of atoms of the portion of the sample. For example, the representation of the crystal structure may consist of spatially arranged green and blue spheres representing the spatial arrangement of the atoms of a first region of the portion of the sample, whereas spatially arranged red and yellow spheres represent the spatial arrangement of atoms of a second region of the portion of the sample, wherein the first and second regions differ with respect to the determined crystallographic properties. Other colors may be used, as well.

At last, the representation of the crystal structure is visualized in the image. The image may be displayed on a monitor, screen or the like.

The electron beam may include electrons having kinetic energies in a range of 10 keV to 30 keV, in particular 15 keV to 25 keV. In particular, the charged particles of the charged particle beam directed to the first locations and the electrons of the electron beam directed to the second locations may have the same or similar energy.

According to an exemplary embodiment, at least one of the directing of the charged particle beam to the first locations, the detecting of the intensities and the visualizing of the representation of the portion of the sample is performed if the zoom parameter is less than the predetermined first threshold value.

According to an exemplary embodiment, at least one of the directing of the electron beam to the second locations, the detecting of diffraction patterns, the determining of the crystallographic properties, the generating of the representation of the crystal structure and the visualizing of the representation of the crystal structure is performed if the zoom parameter is greater than the predetermined second threshold value.

According to an exemplary embodiment, the determining of the crystallographic properties includes identifying and indexing Kikuchi bands based on the two-dimensional spatial distributions. In this embodiment, the diffraction patterns include Kikuchi bands corresponding to straight-line shaped, annular-shaped and elliptically-shaped regions of high intensity of the diffracted electrons on the detection area. These Kikuchi bands may be identified by analyzing the two-dimensional spatial distributions of intensities of diffracted electrons with respect to the aforementioned shapes such as straight lines, annular lines and elliptically-shaped lines. For this, a Hough transformation of the two-dimensional intensity distribution representing the two-dimensional spatial distribution of intensities may be performed. The indexing of Kikuchi bands may include comparing the identified regions of high intensity and their arrangement relative to each other to predetermined Kikuchi band patterns corresponding to a plurality of crystallographic properties of model crystal structures.

According to an exemplary embodiment, the generating of the representation of the crystal structure includes determining mutually exclusive sets of second locations based on a similarity condition for crystallographic properties; determining, for each set of the sets, set-specific properties representing crystallographic properties based on the crystallographic properties of the second locations of the set; and generating the representation of the crystal structure based on the set-specific properties of the sets.

In this embodiment, the second locations are grouped into mutually exclusive sets, i.e. each of the second locations may only be a member of one of the sets. The similarity condition is used to evaluate the crystallographic properties of the second locations and to determine the sets. For example, the sets are determined so that the crystallographic properties of the second locations within each set are similar. In particular, the sets are determined so that neighboring second locations of different sets differ with respect to their crystallographic properties by a predetermined minimum value.

The second locations of each set may be contained within a closed region and the similarity condition may be selected so that the crystallographic properties of the second locations of each set vary by less than a selected limit. Therefore, each set contains only those second locations contained within a closed region, the crystallographic properties of which are similar with respect to each other in that the crystallographic properties vary by less than the selected limit. In particular, the selected limit may be determined based on the crystallographic properties of the second locations of the respective set. For example, if the crystallographic properties at each second location are regarded as the crystal lattice type, a set may include those second locations, the crystal lattice types of which is the same. If, for example, the crystallographic properties are regarded as an orientation of a crystal lattice of the crystal structure at a particular second location, the set may include only those second locations, the orientations of which crystal lattices are similar, e.g. vary within the selected limit. The selected limit may also be a predetermined limit such as angular values representing the limits within which orientations of the crystal lattice of second locations are considered similar according to the similarity condition. The limits may amount to 1°, 0.5°, 0.1° or 0.01°.

The determining of the set-specific properties may be regarded as to determine crystallographic properties representative for each of the determined sets. The set-specific properties represent crystallographic properties and may in particular be crystallographic properties. For determining the set-specific properties of a set, the crystallographic properties of the second locations of the set may be evaluated. For example, one of the crystallographic properties of the second locations of the set may be determined as the set-specific properties of the set. Alternatively, the set-specific properties of a set may be determined based on the crystallographic properties of the second locations of the set, for example, by averaging the crystallographic properties of the second locations of the set. In particular, if the crystallographic properties are regarded as a crystal lattice type, the set-specific properties may be the crystal lattice type of any of the second locations of the set. Alternatively, if the crystallographic properties are regarded as an orientation of a crystal lattice, the set-specific properties may be an averaged orientation of the orientations of the crystal lattices at the second locations of the set. Furthermore, if the crystallographic properties are regarded as both the crystal lattice type and the orientation of the crystal lattice, the set-specific properties may be a combination of the aforementioned possibilities. Therefore, having determined the set-specific properties of the sets, each set may have its own set-specific properties such as crystal lattice type and orientation of the crystal lattice, representative for all second locations of the particular set.

According to an exemplary embodiment, the generating of the representation of the crystal structure includes determining, for each set of the sets, a spatial arrangement of bodies representing the crystal structure at the second locations of the set based on the set-specific properties of the set.

According to this embodiment, a spatial arrangement of bodies such as spheres, cubes, circles, squares and the like is determined according to the set-specific properties of each set. For example, assuming the set-specific properties to represent a crystal lattice type and an orientation of a crystal lattice, the spatial arrangement of bodies may be calculated according to the crystal lattice type and the orientation of the crystal lattice according to the crystal lattice type throughout all second locations of the set. In particular, the spatial arrangement may be calculated such that, throughout all second locations of the set, a repetitive pattern of bodies is determined. That is, within a region defined by the second locations of each set a repetitive pattern of bodies represents the crystal structure within the region according to the set-specific properties of the set.

According to an exemplary embodiment, the method further includes changing the zoom parameter from a value less than the predetermined first threshold value to a value greater than the predetermined second threshold value. In particular, the method includes changing the zoom parameter from a value less than the predetermined second threshold value to a value greater than the predetermined first threshold value. Therefore, both a representation of the portion of the sample and a representation of the crystal structure of the portion are visualized in images.

According to a second aspect, an embodiment of a method of generating a zoom sequence visualizing a portion of a sample is similar to the embodiments described above and reference is made to the description of the embodiments above, however, the directing of the charged particle beam to the first locations and the directing of the electron beam to the second locations are performed using predetermined scan resolutions which are independent of the zoom parameter. Furthermore, the directing of the charged particle beam to the first locations, the directing of the electron beam to the second locations, the detecting of intensities and the detecting of diffraction patterns are performed before the changing of the zoom parameter.

Such a method of generating a zoom sequence visualizing a portion of a sample may include directing a charged particle beam to first locations of a portion of a sample using a charged particle beam system, detecting intensities representing amounts of particles incident onto a detection area during the directing of the charged particle beam to the first locations, directing an electron beam to second locations of the portion of the sample using a scanning electron microscope, detecting diffraction patterns generated during the directing of the electron beam to the second locations using the scanning electron microscope, determining crystallographic properties of a crystal structure of the portion of the sample for each of the second locations based on the detected diffraction patterns, generating a representation of the crystal structure of the portion of the sample based on the determined crystallographic properties; changing a zoom parameter representing a magnification of an image of the portion of the sample; visualizing a representation of the portion of the sample in the image based on image data representing the intensities if the zoom parameter is less than a predetermined first threshold value; and visualizing the representation of the crystal structure in the image if the zoom parameter is greater than a predetermined second threshold value.

According to this embodiment, a measurement part of the method, i.e. the directing of the charged particle beam to the first locations, the directing of the electron beam to the second locations, the detecting of the intensities and the detecting of the diffraction patterns may be performed independently of a visualizing part of the method. In particular, the measurement part and the visualizing part may be performed by different systems. For example, the measurement part may be performed by a suitable microscope system, whereas the visualizing part may be performed by a suitable personal computer and the like. In particular, the measurement part may be performed and be finished before visualizing the data measured during the measurement part.

According to an exemplary embodiment, the first locations and/or the second locations are selected prior to selecting the zoom parameter and prior to the changing of the zoom parameter. Therefore, the first locations and/or the second locations are selected independently of the zoom parameter. In particular, the scan resolution used during the directing of the charged particle beam to the first locations and during the directing of the electron beam to the second locations are selected independently of the zoom parameter.

According to an exemplary embodiment, the generating of the representation of the crystal structure is performed if the zoom parameter is greater than the predetermined second threshold value.

Reference is made to the description of the exemplary embodiments according to the first aspect, in particular to the description of the charged particle beam, the charged particle beam system, the individual steps of the method, etc.

According to a third aspect, an embodiment of a method of generating a zoom sequence visualizing a portion of a sample includes changing a zoom parameter representing a magnification of an image of a portion of a sample; visualizing a representation of the portion of the sample in the image based on first data representing intensities associated with plural distinct first locations of the portion of the sample if the zoom parameter is less than a predetermined first threshold value; generating a representation of a crystal structure of the portion of the sample based on second data representing crystallographic properties of the crystal structure, wherein the crystallographic properties are associated with plural distinct second locations of the portion of the sample; visualizing the representation of the crystal structure of the portion of the sample in the image if the zoom parameter is greater than a predetermined second threshold value.

According to an exemplary embodiment, the method further includes: determining the crystallographic properties of the crystal structure of the portion of the sample for each of the second locations based on data representing diffraction patterns, in particular two-dimensional diffraction patterns, of the sample. The determining of the crystallographic properties may be performed if the zoom parameter is greater than a predetermined second threshold value.

Reference is made to the description of the exemplary embodiments according to the first and second aspects which may also apply to the second aspect.

According to a fourth aspect, an embodiment is a microscope system configured to perform at least one of the methods described above.

An exemplary embodiment of a microscope system may be configured to generate a zoom sequence visualizing a portion of a sample at a magnification according to a zoom parameter in an image, to direct a charged particle beam to first locations of the portion of the sample based on the zoom parameter, to detect intensities representing amounts of particles incident onto a detection area of at least one detector while directing the charged particle beam to the first locations, to visualize a representation of the portion of the sample in the image based on image data representing the intensities, wherein visualizing of the representation based on the image data is performed if the zoom parameter is less than a predetermined first threshold value; to direct an electron beam to second locations of the portion of the sample based on the zoom parameter, to detect diffraction patterns generated while directing the electron beam to the second locations by at least one electron detector, to determine crystallographic properties of a crystal structure of the portion of the sample for each of the second locations based on the detected diffraction patterns, to generate a representation of the crystal structure of the portion of the sample based on the determined crystallographic properties, to visualize the representation of the crystal structure in the image, wherein visualizing of the representation of the crystal structure is performed if the zoom parameter is greater than a predetermined second threshold value.

BRIEF DESCRIPTION OF THE DRAWINGS

The foregoing as well as other advantageous features of the disclosure will be more apparent from the following detailed description of exemplary embodiments of the disclosure with reference to the accompanying drawings, in which.

DETAILED DESCRIPTION

Figure 1:
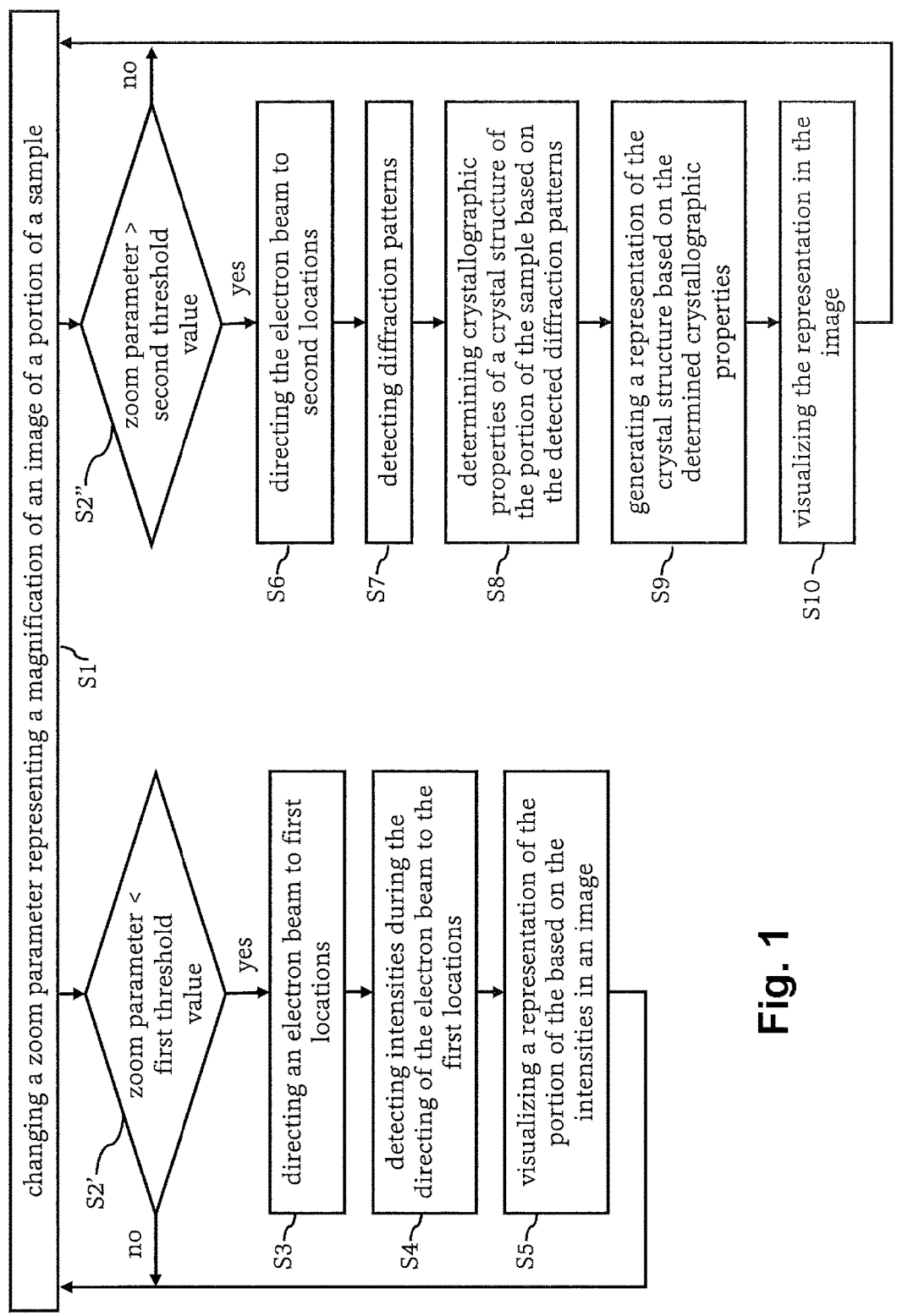
FIG. 1 shows a flowchart illustrating a method of generating a zoom sequence according to a first aspect.
Figures 3A, 3B, 3C:
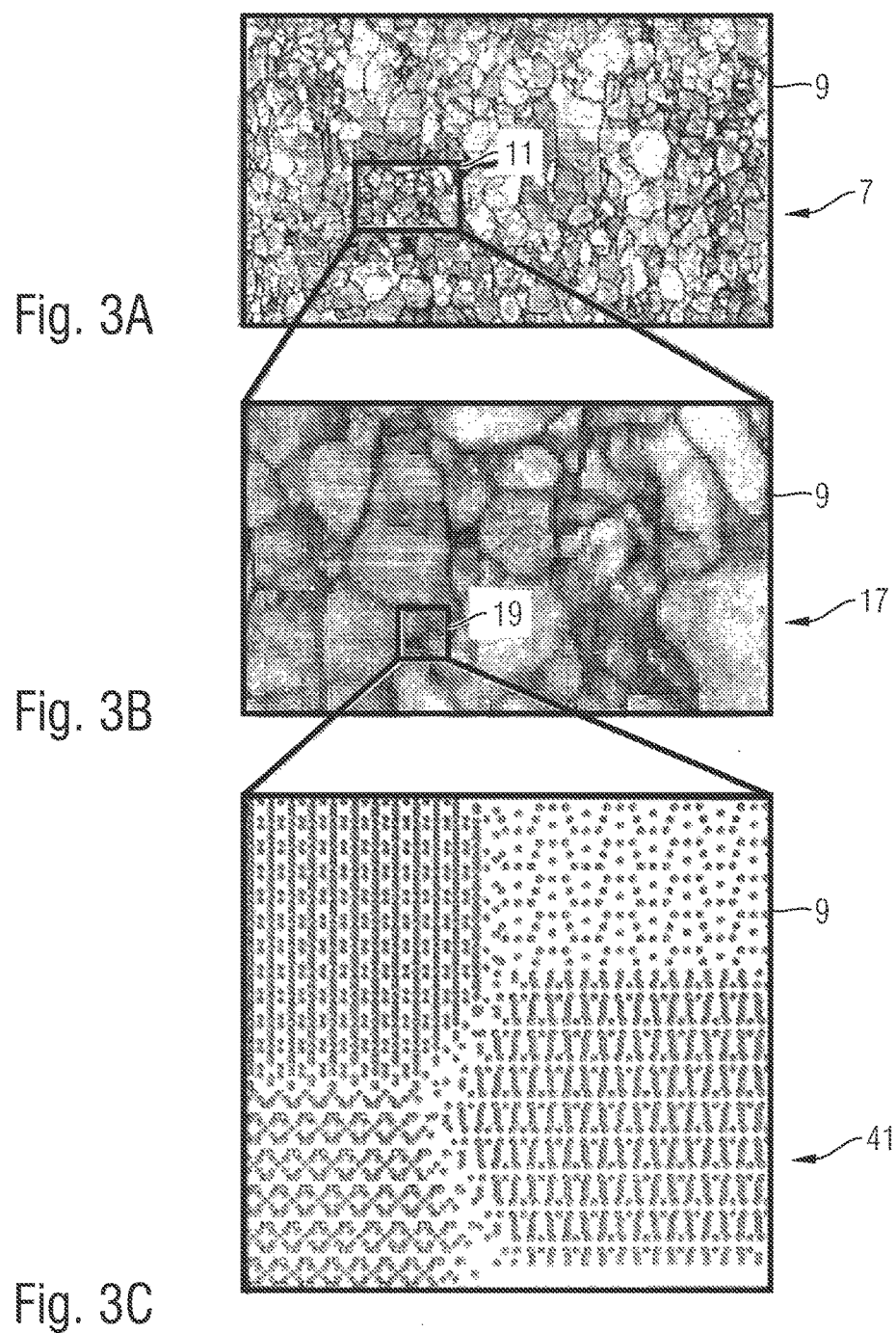
FIG. 3A shows a schematic illustration of a representation of a portion of the sample at a first value of a zoom parameter in an image.
FIG. 3B shows a schematic illustration of a representation of a portion of the sample at a second value of the zoom parameter being greater than the first value in the image.
FIG. 3C shows a schematic illustration of a crystal structure of a portion of the sample corresponding to a third value of the zoom parameter being greater than the second value in the image.

FIG. 1 shows a flowchart illustrating a method of generating a zoom sequence visualizing a portion of a sample in an image. Such a sequence is illustrated in FIGS. 3A to 3C.

First, in step S1, the zoom parameter representing a magnification of the image is changed (or initially defined). Subsequently, in step S2', it is determined whether the zoom parameter is less than a predetermined first threshold value. If the zoom parameter is less than the predetermined first threshold value, the method proceeds to step S3, otherwise to step S1. In parallel, in step S2", it is determined whether the zoom parameter is greater than a predetermined second threshold value. If the zoom parameter is greater than the predetermined second threshold value, the method proceeds to step S6, otherwise to step S1. The predetermined first and second threshold values may represent a zoom parameter in a range about a maximum spatial resolution for which sharp representations of the portion of the sample may be determined using a charged particle beam system, in particular a scanning electron microscope or an ion beam microscope.

If the zoom parameter is less than the predetermined first threshold value, a representation of the portion of the sample is visualized according to the steps S3 to S5. If the zoom parameter is greater than the predetermined second threshold value, a representation of the crystal structure of a portion of the sample is visualized according to the steps S6 to S10. When analyzing a sample, usually a small zoom parameter less than the predetermined first and second threshold values is first selected to examine a rather large portion of the sample. Accordingly, steps S3 to S5 are first described with reference to FIGS. 1, 2 and 3A to 3C, assuming a zoom parameter less than the predetermined first threshold value.

Figure 2:
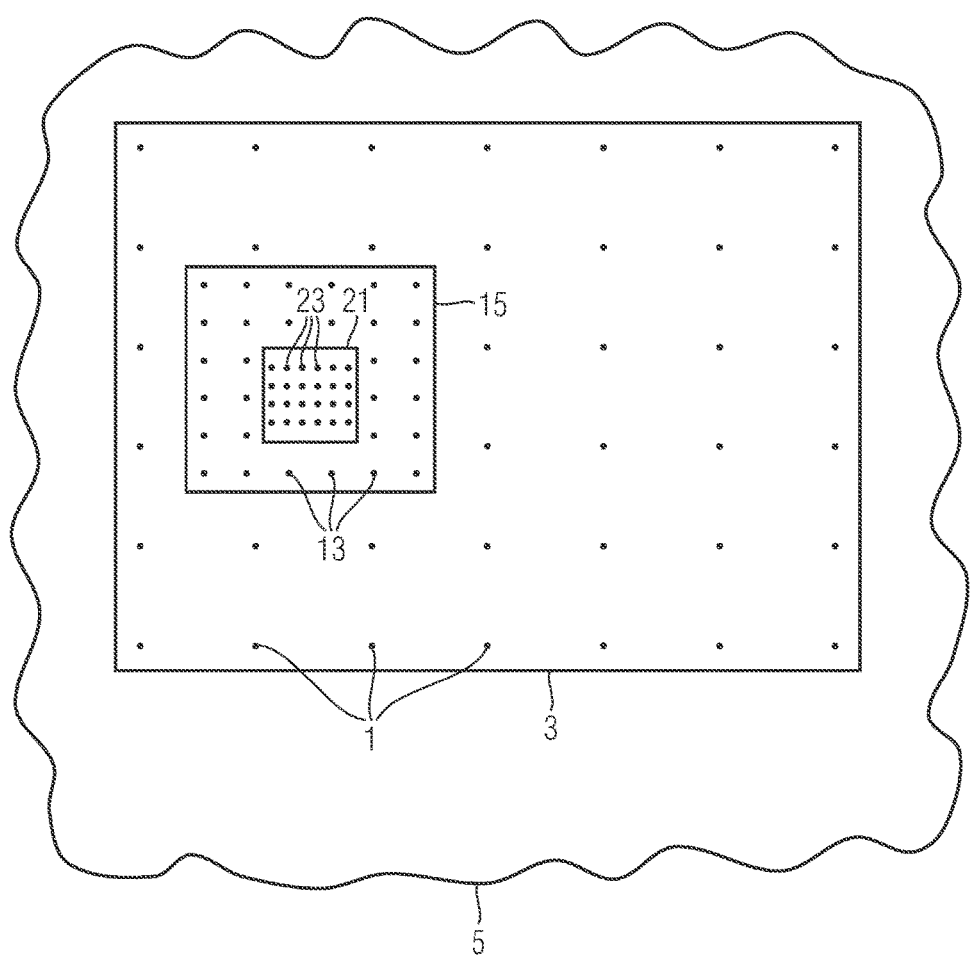
FIG. 2 shows locations of incidence of an electron beam onto a sample according to the method of FIG. 1.

In S3, illustrated in FIG. 1, an electron beam is directed to first locations 1 of a portion 3 of a sample 5, illustrated in FIG. 2, based on the zoom parameter using a scanning electron microscope. The directing of the electron beam is performed so that the first locations 1 are arranged in a regular array of the portion 3. The size of the portion 3 is defined by the first locations 1 and may be selected by choosing the zoom parameter accordingly. A spatial frequency representing a distance between the first locations 1, i.e. a scan resolution, is selected based on the zoom parameter.

According to step S4, during the directing of the electron beam to the first locations 1, intensities representing amounts of electrons emitted from the first locations and being incident onto a detection area of an electron detector are detected. The amount of electrons emitted from the first locations and being incident onto the detection area depends on the structure of the sample at the first locations 1 and, therefore, is suitable to characterize the sample at the first locations 1.

According to step S5, a representation 7 of the portion 3 of the sample 5 is visualized in an image 9, illustrated in FIG. 3A, based on image data representing the detected intensities. In the image 9, i.e. in the representation 7 of the portion 3, bright areas correspond to areas of high amounts of detected electrons, whereas dark areas correspond to areas of low amounts of detected electrons. After completion of the visualization, the method proceeds to step S1.

Assuming that a region of interest 11 has been identified in the image 9 visualizing the representation 7 of the portion 3 of the sample 5, the zoom parameter is increased to a second value greater than the first value but yet less than the predetermined first and second threshold values. This involves changing the zoom parameter according to step S1 of FIG. 1. Then, the method proceeds to steps S2' and S2" and it is again determined whether the zoom parameter is less than the predetermined first threshold value and whether the zoom parameter is greater than the predetermined second threshold value. As the second value is again less than the predetermined first and second threshold values, the steps S3 to S5 are repeated using the second value for the zoom parameter.

Accordingly, in step S3, the electron beam is directed to first locations 13 of the portion 15 of the sample 5, illustrated in FIG. 2. Due to the new value, i.e. the second value, for the zoom parameter, the directing of the electron beam is performed based on the second value of the zoom parameter. The increasing of the zoom parameter results in a higher scanning resolution, i.e. the distance between the first locations 13 is decreased and the portion 15 of the sample to be visualized is decreased in size, compared to the preceding scanning using the first value for the zoom parameter. Also, the center of the portion 15 may be displaced from the center of the portion 3 by accordingly directing the electron beam onto the sample.

According to step S4, intensities are detected, as before, during the directing of the electron beam to the first locations 13. Subsequently, in step S5, a representation 17 of the portion 15 of the sample 5 is visualized in the image 9 based on the detected intensities, illustrated in FIG. 3B. As the scanning resolution during the directing of the electron beam to the portion 15 is greater than the scanning resolution during the directing of the electron beam to the portion 3, the representation 17 of the portion 15 appears magnified compared to the representation 7 of the portion 3, assuming an image 9 of the same size.

In the embodiment described hereinbefore, electrons of an electron beam were used to detect intensities representing a local property of the sample 5. However, other charged particles beams and suitable detectors may be used instead or in addition. For example, an ion beam of ions may be used to determine the intensities representing the local property of the sample 5.

When analyzing the representation 17, a region of interest 19 may be identified. Therefore, the zoom parameter may be increased to a third value greater than the second value in order to obtain a magnified image of a portion 21 of the sample 5 illustrated in FIG. 2. This involves changing the zoom parameter according to step S1. Subsequently in steps S2' and S2", it is decided whether the zoom parameter is less than the predetermined first threshold value and whether the zoom parameter is greater than the predetermined second threshold value, respectively. Assuming that the third value of the zoom parameter is greater than the predetermined second threshold value, i.e. a maximum magnification which can be provided by the steps S3 to S5 may be exceeded, the method proceeds to step S6.

In step S6, illustrated in FIG. 1, the electron beam is directed to second locations 23 of the portion 21 of the sample 5, illustrated in FIG. 2, based on the zoom parameter using the scanning electron microscope. The second locations 23 may be arranged in a regular array and displaced relative to the first locations, as indicated in FIG. 2. A spatial frequency representing a distance between adjacent second locations, i.e. a scanning resolution, may be selected according to the zoom parameter and be on the order of the scanning resolution in step S3. However, in practice, the scanning resolution used for directing the electron beam to the second locations 23 may be greater than the scanning resolution used for directing the electron beam to the first locations.

Figure 4A:
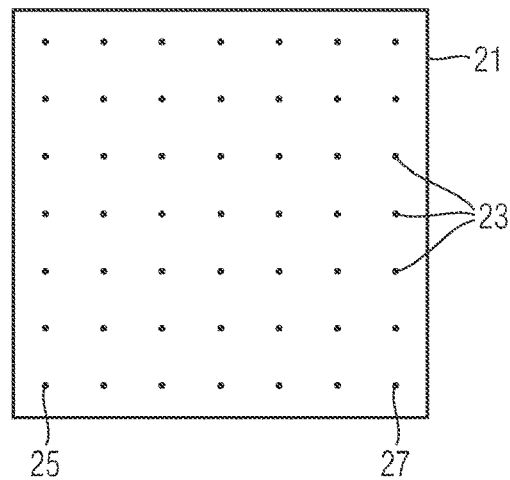
FIG. 4A shows second locations within a portion of the sample.

Steps S7 and S8, illustrated in FIG. 1, are described with reference to FIGS. 4A to 4E. FIG. 4A shows a large-size illustration of the portion 21 containing the second locations 23.

In step S7, diffraction patterns generated during the directing of the electron beam to the second locations 23 are detected using the scanning electron microscope. The diffraction patterns occur due to the interaction of the electron beam with the sample and contain information regarding the structure, in particular the crystal structure, of the sample at the individual (second) locations, the electron beam is directed to. Therefore, the diffraction patterns may indicate the crystal structure of the sample at the second locations 23. Due to the large size of the interaction volume, the crystal structure cannot be resolved using the steps S3 to S5.

Figure 4B:
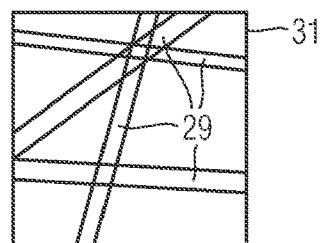
FIGS. 4B and 4C show diffraction patterns associated with different second locations of FIG. 4A.
Figure 4C:
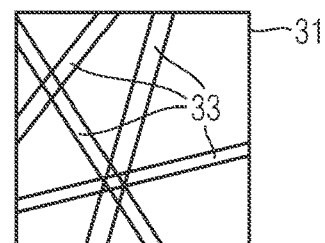

FIG. 4B shows a diffraction pattern detected for a second location 25, illustrated in FIG. 4A. Similarly, FIG. 4C shows a diffraction pattern detected for a second location 27, illustrated in FIG. 4A. The diffraction patterns include a plurality of band-shaped regions 29 and 33 corresponding to Kikuchi bands. The diffraction patterns may also include annular-shaped or elliptically-shaped regions not illustrated in FIG. 4B. The regions 29 and 33 correspond to regions of high intensity of electrons incident onto the detection area 31.

The relative orientation of the regions 29 is indicative for crystallographic properties of the sample at the second location 25. Similarly, the relative orientation of the regions 33 is indicative for crystallographic properties of the sample at the second location 27. The crystallographic properties may include, for example, a crystal lattice type representing a crystal lattice of the crystal structure and an orientation of the crystal lattice relative to a reference coordinate system. In particular, the relative orientation of the regions 29 may correspond to a crystal lattice of the crystal structure of the sample 5 at the second location 25 and the relative orientation of the regions 33 may correspond to a crystal lattice of the crystal structure of the sample 5 at the second location 27. As the diffraction patterns illustrated in FIGS. 4B and 4C are different, the crystallographic properties, in particular the crystal lattice types and/or orientations of the crystal lattices represented by the crystal lattice types, of the crystal structure of the sample are different at the second locations 25 and 27, i.e. the crystal structure of the sample 5 has different crystallographic properties at the second locations 25 and 27.

In step S8, illustrated in FIG. 1, the crystallographic properties of the crystal structure of the portion 21 of the sample 5 are determined for each of the second locations 23 based on the detected diffraction patterns. Therefore, crystallographic properties may be associated with each of the second locations 23.

Figure 4D:
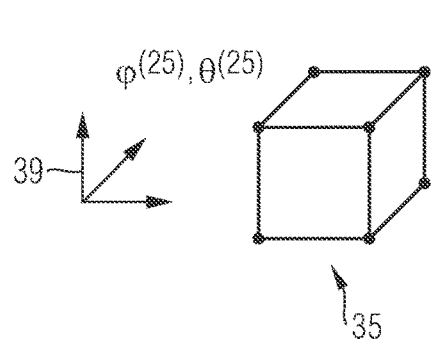
FIGS. 4D and 4E show a representation of crystallographic properties associated with the diffraction patterns of FIGS. 4B and 4C.
Figure 4E:
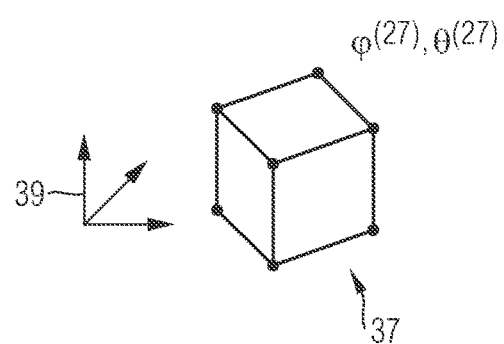

Exemplary crystallographic properties determined based on the diffractions patterns illustrated in the FIGS. 4B and 4C are shown in FIGS. 4D and 4E, respectively. As illustrated by the cubic shapes 35 and 37 of the FIGS. 4D and 4E, the crystal lattice type determined based on the diffraction patterns of the locations 25 and 27 are cubic. Other possible values for the crystal lattice type are face-centered-cubic or body-centered-cubic or any other of the Bravais lattices. In addition, the orientation $\varphi$, $\theta$ of the crystal lattice represented by the cubic shapes 35 and 37 relative to the reference coordinate system 39 are determined based on the diffraction patterns. In particular, an orientation $\varphi^{(25)}$, $\theta^{(25)}$ is determined for the orientation of the crystal lattice at the second location 25. Similarly, an orientation $\varphi^{(27)}$, $\theta^{(27)}$ is determined for the orientation of the crystal lattice at the second location 27.

Accordingly, the crystallographic properties of each of the second locations 23 include the crystal lattice type and the orientation of the crystal lattice represented by the crystal lattice type. Based on the crystallographic properties, a representation of the crystal structure, in particular a spatial arrangement of atoms of the sample, for example in a grain of the sample, may be generated as described below in steps S9 and S10.

Additional information such as a chemical composition of the sample, i.e. the different chemical elements of the sample, may also be determined. In particular, the additional information may be determined at the second locations 23 to complement the crystallographic properties for each of the second locations 23. For example, the chemical composition may be determined by acquiring X-ray spectra at each of the second locations 23 and subsequently analyzing the X-ray spectra in order to determine characteristic features of the X-ray spectra corresponding to a particular chemical element.

Steps S9 and S10, illustrated in FIG. 1, are illustrated with reference to FIG. 3C. In step S9, a representation of the crystal structure of the portion 21 (illustrated in FIGS. 2 and 4A) of the sample 5 is generated based on the determined crystallographic properties of the second locations 23. In this embodiment, the representation corresponds to a spatial arrangement of bodies representing the crystal structure at the second locations of the portion 21 wherein the spatial arrangement is determined in accordance with the crystallographic properties at the individual second locations 23. Subsequently, the representation is visualized in step S10. After completion of the visualization, the method proceeds to step S1. FIG. 3C shows a representation 41 of the crystal structure of the portion 21 in the image 9. The image shows the spatial arrangement of bodies representing the atoms of the crystal structure of the portion 21 of the sample 5.

Another exemplary embodiment of the method of generating a zoom sequence visualizing a portion of a sample is described in the following. The method according to this embodiment essentially corresponds to the method of the embodiment described hereinbefore. However, step S9 now includes steps S11 to S13 illustrated in FIG. 5. Accordingly, step S9 includes determining mutually exclusive sets of second locations based on a similarity condition for crystallographic properties.

Figure 6A:
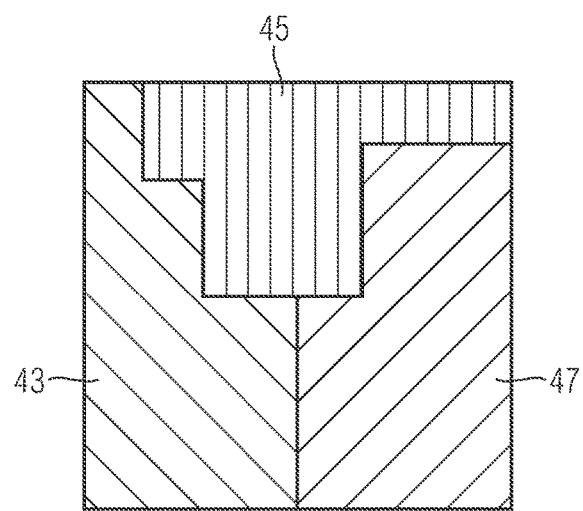
FIG. 6A shows sets of second locations within the portion of the sample of FIG. 4A.

FIG. 6A systematically shows three mutually exclusive sets 43, 45 and 47, each of which contains some of the second locations 23 illustrated in FIG. 4A. The sets 43, 45 and 47 correspond to regions of the portion 21 of the sample 5 having similar crystallographic properties. For example, the crystal lattice type at the second locations of the set 43 are the same, whereas the crystal lattice type of the second locations of the set 45 are also the same, however different from the crystal lattice type of the second locations of the set 43. Similarly, the crystal lattice type of the second locations of the set 47 are the same, however different from the crystal lattice type of the sets 43 and 45.

According to another example, the orientation of the crystal lattices at the second locations of the set 43 are similar, i.e. vary within a selected limit. Similarly, the orientation of the crystal lattices at the second locations of the set 45 are similar and the orientation of the crystal lattices at the second locations of the set 47 are similar according to similarity condition. However, the orientation of the crystal lattice of a second location of the set 43 differs considerably from the orientation of the crystal lattice of a second location of the sets 45 and 47 and so on. The sets are determined such that each set contains second locations within a closed region. In practice, the sets may correspond to regions of the sample of a same grain, whereas those regions where different sets adjoin one another may be grain boundaries.

Figure 5:
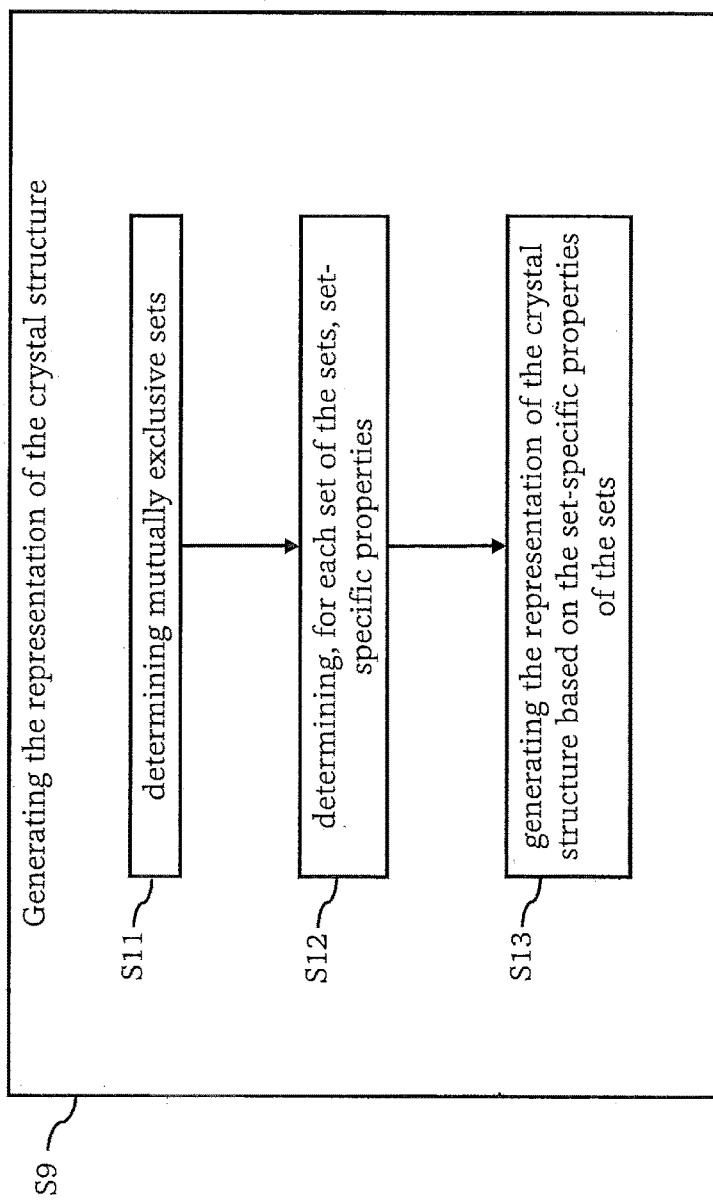
FIG. 5 shows a flowchart which illustrates generating a representation of a crystal structure.

In step S12, illustrated in FIG. 5, for each set of the sets 43, 45 and 47, set-specific properties representing crystallographic properties are determined based on the crystallographic properties of the second locations of each set. For example, the crystallographic properties of the second locations of the set 43 are used to determine the set-specific properties for the set 43. Similarly, the crystallographic properties of the second locations of the set 45 and 47 are used to determine the set-specific properties of the sets 45 and 47, respectively. The set-specific properties may therefore be regarded as the crystallographic properties of a set.

The determining of the set-specific properties may include, for example, selecting the crystallographic properties of one of the second locations of the set and/or averaging the crystallographic properties of a plurality of second locations of the set. For example, the set-specific properties of set 45 may be determined by averaging the crystallographic properties of a plurality of the second locations of the set 45.

Figures 6B, 6C:
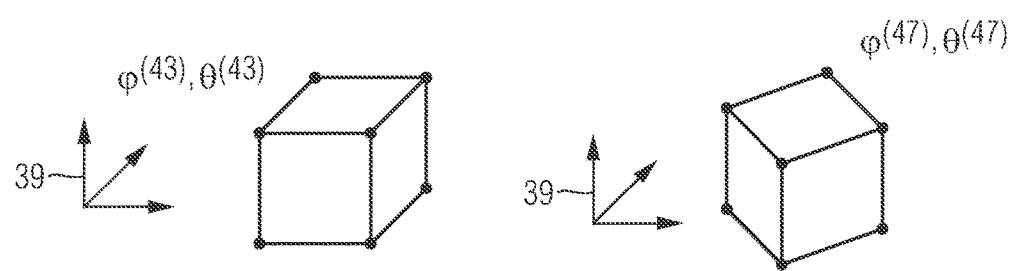
FIGS. 6B and 6C show a representation of set-specific properties associated with different sets of FIG. 6A.

Exemplary set-specific properties of the sets 43 and 47 are illustrated in FIGS. 6B and 6C, respectively. Accordingly, the set-specific properties illustrated in FIG. 6B may be regarded as representative for the crystallographic properties of the second locations of the set 43, whereas the set-specific properties illustrated in FIG. 6C may be regarded as representative for the crystallographic properties of the second locations of the set 47. In particular, an orientation $\varphi^{(43)}$, $\theta^{(43)}$ is determined for the orientation of the crystal lattice of the set 43. Similarly, an orientation $\alpha^{(47)}$, $\theta^{(47)}$ is determined for the orientation of the crystal lattice of the set 47.

In step S13, the representation of the crystal structure is generated based on the set-specific properties of the sets. For example, the set-specific properties illustrated in FIG. 6B are used to generate the representation of the crystal structure of the portion 21 at the second locations of the set 43. Accordingly, the representation of the crystal structure of the entire portion 21 may be constructed from the set-specific properties of the sets 43, 45 and 47.

Such a representation may illustrate the crystal structure of the sample by a spatial arrangement of spheres representing atoms of the sample. The spatial arrangement represents the positions of the individual atoms in the sample. Spheres having different colors may represent atoms of different chemical elements.

Figure 7:
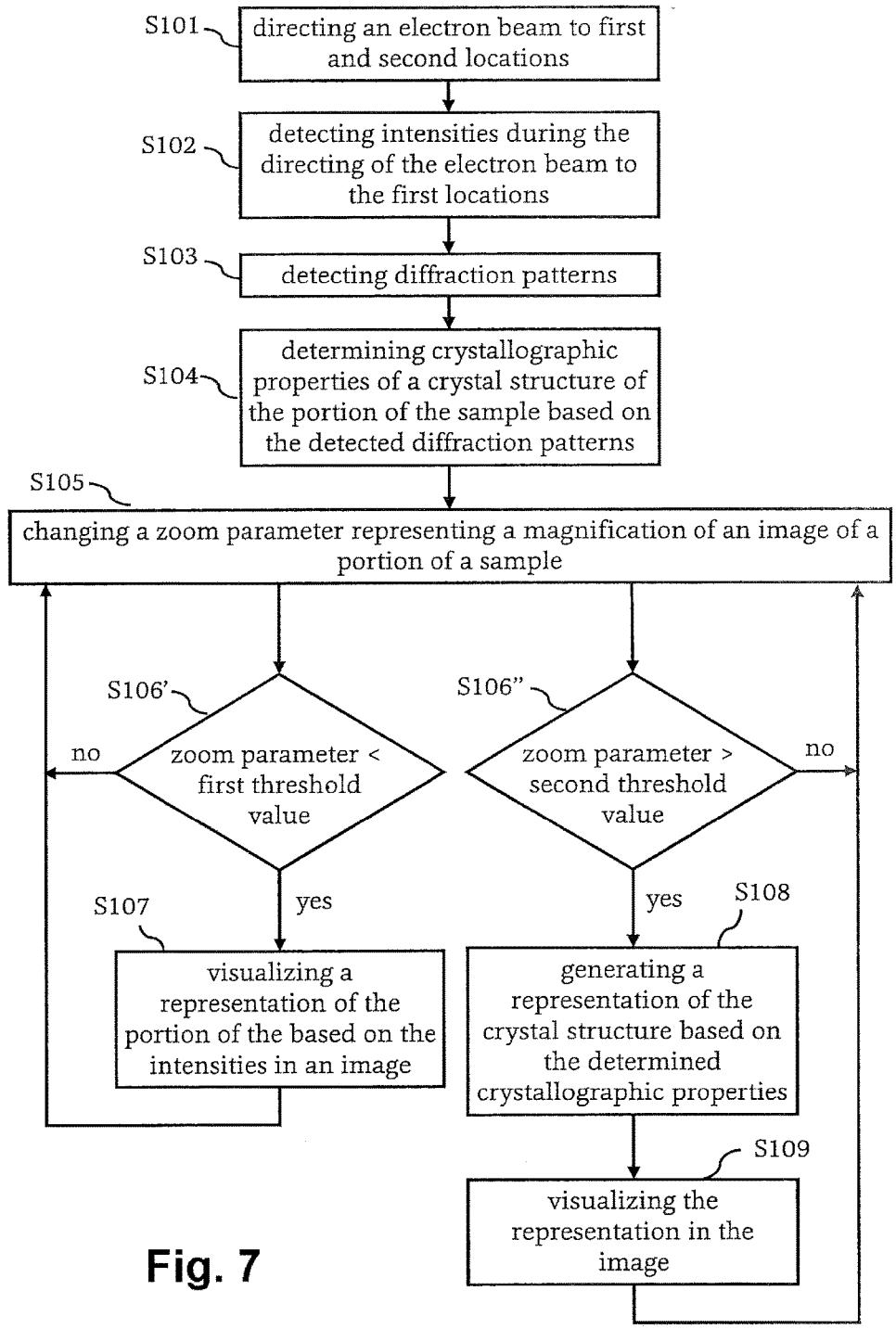
FIG. 7 shows a flowchart illustrating another method of generating a zoom sequence according to a second aspect.

FIG. 7 shows a flowchart illustrating another method of generating a zoom sequence. Similar to the method illustrated in FIG. 1, the method illustrated in FIG. 7 includes changing a zoom parameter representing a magnification of an image of a portion of a sample in step S105, determining whether the zoom parameter is less than a predetermined first threshold value in step S106', determining whether the zoom parameter is greater than a predetermined second threshold value in step S106", directing an electron beam to first locations of the portion of the sample in step S101, detecting intensities during the directing of the electron beam to the first locations in step S102, visualizing a representation of the portion of the sample in the image based on the intensities in step S107, directing the electron beam to second locations of the portion in step S101, detecting diffraction patterns in step S103, determining crystallographic properties of a crystal structure of the portion based on the detected diffraction patterns in step S104, generating a representation of the crystal structure based on the determined crystallographic properties in step S108, and visualizing the representation of the crystal structure in step S109. Therefore, reference is made to the description of the corresponding steps illustrated with reference to FIGS. 1 to 6 above. However, in contrast to the method illustrated in FIG. 1, the order of the steps is changed. Further differences are described below.

Figure 8:
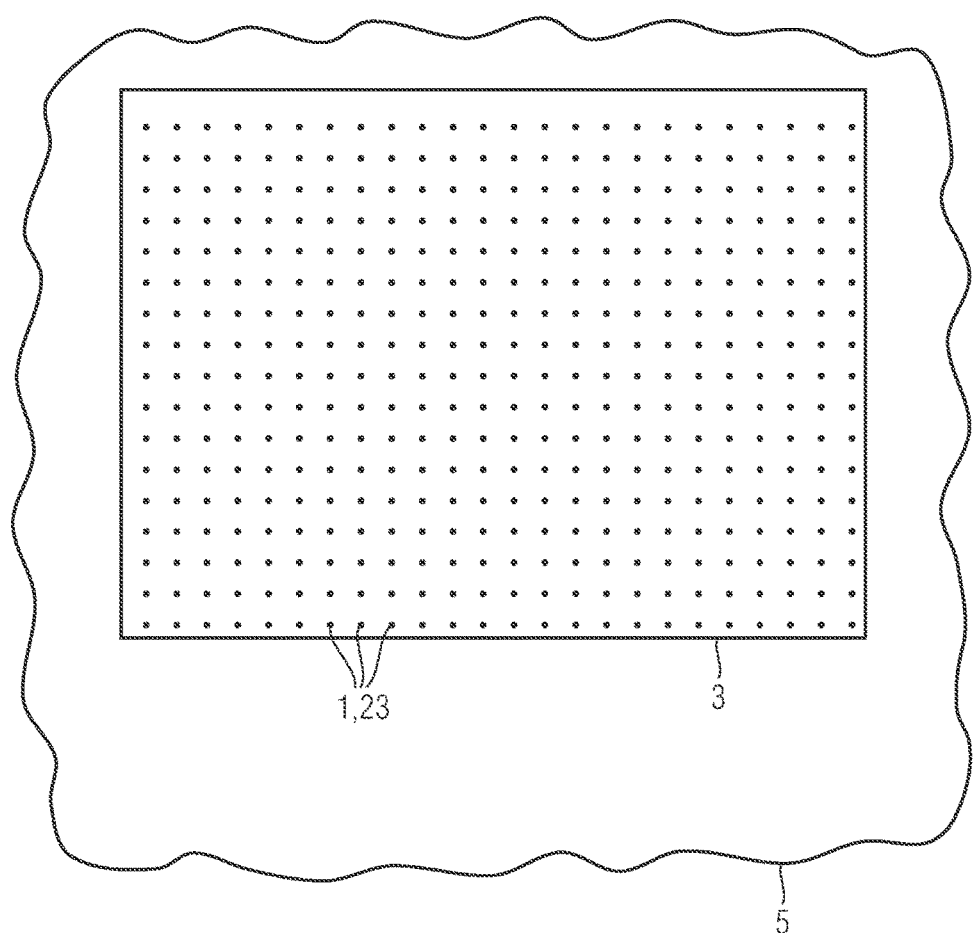
FIG. 8 shows locations of incidence of an electron beam onto a sample according to the method of FIG. 7.

The method illustrated in FIG. 7 is described with reference to FIG. 8 showing locations of incidence of an electron beam onto the sample 5. FIG. 8 corresponds to FIG. 2 of the method illustrated in FIG. 1. In FIG. 8, the portion 3 of the sample 5 corresponds to the portion 3 of FIG. 2, in particular the portions 3 of FIGS. 2 and 8 are of the same size. The locations illustrated by dots within the portion 3 of the sample 5 in FIG. 8 represent first locations 1 and second locations 23. The scan resolution used in the portion 3 of FIG. 8 is much greater compared to the scan resolution used in the portion 3 of FIG. 2. Therefore, a fairly large portion 3 of the sample 5 is scanned at a high scan resolution. The second locations 23 may be selected as to be identical to the first locations 1 as illustrated. However, the second locations 23 may also be selected as to differ from the first locations 1.

When an electron beam is directed to the first locations 1 illustrated in FIG. 8 in step S101, intensities of electrons emerging from the first locations 1, in particular backscattered or secondary electrons, are detected in step S102. As described with reference to the method illustrated in FIG. 1, in general, a charged particle beam, in particular an ion beam, may be directed to the first locations 1 and charged particles emerging from the first locations 1, in particular backscattered or secondary particles, may be detected. These intensities may be used to visualize a representation of the portion 3 or sections of the portion 3 in later steps.

When the electron beam is directed to the second locations 23 illustrated in FIG. 8 in step S101, diffraction patterns are detected in step S103 similar to the step S7. The detecting may be performed using a same detector or different detectors. Explicit reference is made to the description of step S7 of FIG. 1. In contrast to the method described with reference to FIG. 1, diffraction patterns are detected for the fairly large portion 3 of the sample 5 compared to the portion 21 illustrated in FIG. 2.

Subsequently, crystallographic properties of a crystal structure of the portion 3 of the sample 5 for each of the second locations 23 are determined based on the detected diffraction patterns in step S104, similar to step S8. Explicit reference is made to the description of step S8 of FIG. 1. These crystallographic properties may be used to visualize a representation of the crystal structure of the portion 3 or sections of the portion 3 in later steps.

Having performed the steps S101 to S104, an image of the portion 3 of the sample 5 and of sections of the portion 3 may be generated according to the steps S105, S106' and S107 described below. Herein, the step S105 essentially corresponds to the step S1 described with reference to FIG. 1. In step S106', it is determined whether the zoom parameter is less than the predetermined first threshold value. If the zoom parameter is less than the predetermined first threshold value, the method proceeds to step S107, otherwise to step S105. Furthermore, step S107 essentially corresponds to step S5 of FIG. 1. Therefore, if the zoom parameter changed in step S105 is less than the predetermined first threshold value, determined in step S106', a representation of a portion of the sample such as the portion 3 or a section of the portion 3 is visualized based on the previously detected intensities. An exemplary representation 9 is illustrated in FIG. 3A. After completion of the visualization in step S107, the method proceeds to step S105.

In parallel, in step S106", it is determined whether the zoom parameter is greater than the predetermined second threshold value. If the zoom parameter is greater than the predetermined second threshold value, the method proceeds to step S108, otherwise to step S105. Steps S108 and S109 essentially correspond to steps S9 and S10 of FIG. 1. Therefore, if the zoom parameter is greater than the predetermined second threshold value, a representation of the crystal structure is generated and visualized. An exemplary representation of the crystal structure is illustrated in FIG. 3C. After completion of the visualization, the method proceeds to step S105. Therefore, the images 9 illustrated in FIG. 3A to 3C can also be generated by the method of FIG. 7. Explicit reference is made to the description of the steps.

Measurement data representing the intensities and the diffraction patterns may be determined for a fairly large portion of the sample at a high scan resolution and subsequently be stored in a memory. Based on the measurement data stored in memory, a representation of the measurement data may be visualized depending on the zoom parameter. In particular, depending on the zoom parameter, a representation of the intensities and/or a representation of a crystal structure may be generated and visualized. Note that the predetermined scan resolution used to determine the measurement data may be independent of the zoom parameter.

Figure 9:
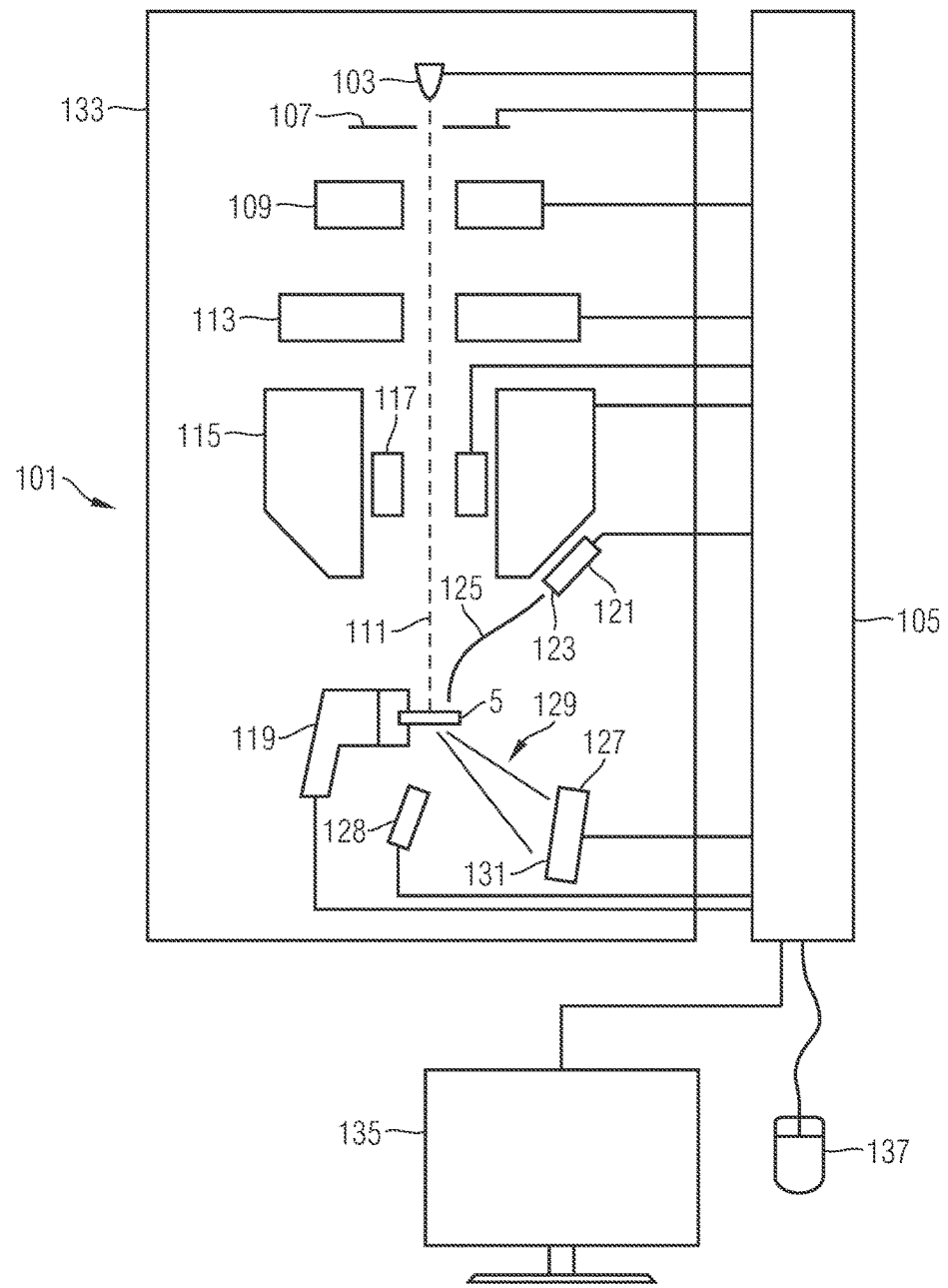
FIG. 9 shows a schematic illustration of a microscope system.

FIG. 9 shows an embodiment of a scanning electron microscope system configured to perform the methods described hereinbefore, in particular the methods according to the first aspect. The scanning electron microscope system 101 includes an electron source 103 configured to emit electrons according to a control signal provided to the electron source 103 by a controller 105. Further, the scanning electron microscope system 101 includes an electrode 107 for accelerating the electrons emitted by electron source 103 according to a control signal provided to a driver of the electrode 107 by the controller 105. The electrons accelerated by the electrode 107 enter a condenser 109 configured to form an electron beam 111 from the electrons entering the condenser 109 and is controlled by the controller 105.

The electron beam 111 next enters a stigmator 113 configured to compensate imaging errors of an objective lens 115 configured to focus the electron beam 111 onto the sample 5. The stigmator 113 and the objective lens 115 are controlled by the controller 105.

The scanning electron microscope system 101 further includes a deflector 117 configured to deflect the electron beam 111 to locations of the sample according to a control signal provided to the deflector 117 by the controller 105. The sample 5 is mounted to a sample mount 119 configured to hold the sample 5 and to position the sample 5 with respect to translational and rotational directions. In particular, the sample is positioned so that the electron beam 111 is incident onto the surface of the sample 5 in a direction substantially orthogonal to the surface onto which the electron beam 111 is incident.

The scanning electron microscope system 101 further includes an electron detector 121, such as a secondary electron detector or a backscattered electron detector, configured to detect intensities of electrons emitted from the sample 5. The electron detector 121 provides a detection signal representing an intensity of electrons incident onto a detection area 123 of the electron detector 121 to the controller 105. Electrons emitted from the sample 5 and being incident onto the detection area 123 of the electron detector 121 are illustrated by numeral 125.

The scanning electron microscope system 101 further includes a spatially resolving electron detector 127, in particular an electron detector spatially resolving in two dimensions, configured to detect diffracted electrons 129 being incident onto a detection area 131 of the electron detector 127. The electron detector 127 is configured to generate detections signals representing a two-dimensional spatial distribution of the intensity of electrons incident onto the detection area 131. The detector 127 transmits the detection signals to the controller 105 configured to determine crystallographic properties of a crystal structure of a portion of the sample 5. The electron detector 127 is disposed on a side of the sample 5 opposite to the side onto which the electron beam 111 is incident. In this case, electrons 129 transmitted through and diffracted by the sample 5 may be detected by the electron detector 127. However, the electron detector 127 may also be disposed on the side of the sample 5 onto which electron beam 111 is incident. In this case, backscattered diffracted electrons may be detected by the electron detector 127. In particular, in order to detect backscattered diffracted electrons, the detection area 131 of the electron detector 127 may be disposed in the vicinity of the objective lens 115 and the sample 5 may be inclined relative to the electron beam 111 so that backscattered diffracted electrons can be incident onto the detection area 131 of the electron detector 127.

Instead of employing two electron detectors as illustrated in FIG. 9, also a single electron detector may be employed. Most of the components of the scanning electron microscope system 101 are disposed in a vacuum chamber 133.

The scanning electron microscope system 101 further includes an X-ray detector 128 configured to detect X-rays emitted from the sample 5. Upon irradiation of the sample 5 with the electron beam 111, X-rays may be emitted from the sample 5 and detected by the X-ray detector 128. The X-ray detector 128 provides a signal representing an X-ray spectrum associated with the location of incidence of the electron beam on the sample to the controller 105 further configured to determine additional properties of the sample 5, such as a chemical composition of the sample 5 at the irradiated first and/or second locations.

The scanning electron microscope system 101 further includes a monitor 135 configured to visualize images generated by the controller 105 and an input device 137 such as a mouse or a keyboard configured to input data to the controller 105, e.g. a zoom parameter representing a magnification of an image to be displayed by the monitor 135.

In particular, a controller 105 is configured to perform any sort of computations or comparisons or the like, to perform the steps S1 to S13 illustrated in FIGS. 1 and 5.

What is claimed is:

1. A method, comprising:
   changing a zoom parameter representing a magnification of an image of a portion of a sample;
   based on the zoom parameter, using a charged particle beam system to direct a charged particle beam to first locations of the portion of the sample;
   detecting intensities representing amounts of particles incident onto a detection area while directing the charged particle beam to the first locations;
   based on image data representing the intensities, visualizing a representation of the portion of the sample in the image when the zoom parameter is less than a predetermined first threshold value;
   based on the zoom parameter, using a scanning electron microscope to direct an electron beam to second locations of the portion of the sample;
   detecting diffraction patterns generated while directing of the electron beam to the second locations;
   for each of the second locations, determining crystallographic properties of a crystal structure of the portion of the sample based on the detected diffraction patterns;
   based on the determined crystallographic properties, generating a representation of the crystal structure of the portion of the sample; and
   visualizing the representation of the crystal structure in the image when the zoom parameter is greater than a predetermined second threshold value,
   wherein:
      generating the representation of the crystal structure comprises:
         determining mutually exclusive sets of the second locations based on a similarity condition for crystallographic properties;
         for each set of the sets, determining set-specific properties representing crystallographic properties based on the crystallographic properties of the second locations of the set; and
         generating the representation of the crystal structure based on the set-specific properties of the sets; and
      the similarity condition is selected so that, for each set of the sets, the crystal lattice types of all second locations of the set are the same and the orientations of all second locations of the set vary by less than 1°.

2. The method of claim 1, wherein the diffraction patterns are two-dimensional spatial distributions of intensities of diffracted electrons.

3. The method of claim 2, wherein determining the crystallographic properties comprises identifying and indexing Kikuchi bands based on the two-dimensional spatial distributions.

4. The method of claim 1, wherein:
at each location of the second locations:
the crystallographic properties comprise a crystal lattice type representing a crystal lattice of the crystal structure at the location; and
an orientation of the crystal lattice relative to a reference coordinate system; and
determining of the crystal lattice type comprises determining at least one lattice parameter of the crystal lattice.

5. The method of claim 1, wherein:
the second locations of each set are contained within a closed region; and
the similarity condition is selected so that the crystallographic properties of the second locations of each set vary by less than a selected limit.

6. The method of claim 1, wherein:
the second locations of each set are contained within a closed region; and
the similarity condition is selected so that the crystallographic properties of the second locations of each set vary by less than a selected limit determined based on the crystallographic properties of the second locations of each set.

7. The method of claim 1, wherein at least one of the following holds:
a) the crystallographic properties at each location of the second locations comprise:
a crystal lattice type representing a crystal lattice of the crystal structure at the location; and
an orientation of the crystal lattice relative to a reference coordinate system; and
b) for each set of the sets, the set-specific properties comprise:
one of the crystallographic properties of the second locations of the set; and/or
averaged crystallographic properties of the crystallographic properties of the second locations of the set.

8. The method of claim 7, wherein a) and b) hold.

9. The method of claim 1, wherein the crystallographic properties at each location of the second locations comprise:
a crystal lattice type representing a crystal lattice of the crystal structure at the location; and
an orientation of the crystal lattice relative to a reference coordinate system.

10. The method of claim 1, wherein for each set of the sets, the set-specific properties comprise:
one of the crystallographic properties of the second locations of the set; and/or
averaged crystallographic properties of the crystallographic properties of the second locations of the set.

11. The method of claim 1, wherein:
generating the representation of the crystal structure comprises determining, for each set of the sets, a spatial arrangement of bodies representing the crystal structure at the second locations of the set based on the set-specific properties of the set; and the spatial arrangement of the bodies for each set is a repetitive pattern of bodies.

12. The method according of claim 1, further comprising changing the zoom parameter from a value that is less than the predetermined first threshold value to a value that is greater than the predetermined second threshold value.

13. A microscope system, wherein the microscope system is configured to:
generate a zoom sequence visualizing a portion of a sample at a magnification according to a zoom parameter in an image;
based on the zoom parameter, direct a charged particle beam to first locations of the portion of the sample;
while directing the charged particle beam to the first locations, detect intensities representing amounts of particles incident onto a detection area of a first detector;
based on image data representing the intensities, visualize a representation of the portion of the sample in the image when the zoom parameter is less than a predetermined first threshold value;
based on the zoom parameter, direct an electron beam to second locations of the portion of the sample;
use a second detector to detect diffraction patterns generated while directing the electron beam to the second locations, the second detector being different from the first detector;
based on the detected diffraction patterns, determine crystallographic properties of a crystal structure of the portion of the sample for each of the second locations;
based on the determined crystallographic properties, generate a representation of the crystal structure of the portion of the sample; and
visualize the representation of the crystal structure in the image when the zoom parameter is greater than a predetermined second threshold value,
wherein:
the microscope system is configured so that generating the representation of the crystal structure comprises:
determining mutually exclusive sets of the second locations based on a similarity condition for crystallographic properties;
for each set of the sets, determining set-specific properties representing crystallographic properties based on the crystallographic properties of the second locations of the set; and
generating the representation of the crystal structure based on the set-specific properties of the sets; and
the similarity condition is selected so that, for each set of the sets, the crystal lattice types of all second locations of the set are the same and the orientations of all second locations of the set vary by less than 1°.

14. A method, comprising:
using a charged particle system to direct a charged particle beam to first locations of a portion of a sample using a charged particle beam system;
while directing the charged particle beam to the first locations, detecting intensities representing amounts of particles incident on a detection area;
using a scanning electron microscope to direct an electron beam to second locations of the portion of the sample;
detecting diffraction patterns generated while directing the electron beam to the second locations;
based on the detected diffraction patterns, determining crystallographic properties of a crystal structure of the portion of the sample for each of the second locations;

based on the determined crystallographic properties, generating a representation of the crystal structure of the portion of the sample;

changing a zoom parameter representing a magnification of an image of the portion of the sample;

based on image data representing the intensities, visualizing a representation of the portion of the sample in the image when the zoom parameter is less than a predetermined first threshold value; and visualizing the representation of the crystal structure in the image when the zoom parameter is greater than a predetermined second threshold value, wherein:
  generating the representation of the crystal structure comprises:
    determining mutually exclusive sets of the second locations based on a similarity condition for crystallographic properties;
    for each set of the sets, determining set-specific properties representing crystallographic properties based on the crystallographic properties of the second locations of the set; and
    generating the representation of the crystal structure based on the set-specific properties of the sets; and
  the similarity condition is selected so that, for each set of the sets, the crystal lattice types of all second locations of the set are the same and the orientations of all second locations of the set vary by less than 1°.

15. The method according to claim 14, wherein the method comprises at least one of the following:
  selecting at least one of the first locations and the second locations prior to the changing of the zoom parameter; and
  selecting at least one of the first locations and the second locations independently of the zoom parameter; and
  generating the representation of the crystal structure when the zoom parameter is greater than the predetermined second threshold value.

16. A method, comprising:
  changing a zoom parameter representing a magnification of an image of a portion of a sample;
  when the zoom parameter is less than a predetermined first threshold value, visualizing a representation of the portion of the sample in the image based on first data representing intensities associated with plural distinct first locations of the portion of the sample;
  generating a representation of a crystal structure of the portion of the sample based on second data representing crystallographic properties of the crystal structure, the crystallographic properties being associated with plural distinct second locations of the portion of the sample; and
  when the zoom parameter is greater than a predetermined second threshold value, visualizing the representation of the crystal structure of the portion of the sample in the image, wherein:
  generating the representation of the crystal structure comprises:
    determining mutually exclusive sets of the second locations based on a similarity condition for crystallographic properties;
    for each set of the sets, determining set-specific properties representing crystallographic properties based on the crystallographic properties of the second locations of the set; and
    generating the representation of the crystal structure based on the set-specific properties of the sets; and
  the similarity condition is selected so that, for each set of the sets, the crystal lattice types of all second locations of the set are the same and the orientations of all second locations of the set vary by less than 1°.

17. The method according to claim 16, wherein at least one of the following holds:
  the method further comprises determining the crystallographic properties of the crystal structure of the portion of the sample for each of the second locations based on data representing diffraction patterns; and
  determining the crystallographic properties when the zoom parameter is greater than a predetermined second threshold value.

18. The method according to claim 16, further comprising determining the crystallographic properties of the crystal structure of the portion of the sample for each of the second locations based on data representing two-dimensional diffraction patterns.

* * * * *

UNITED STATES PATENT AND TRADEMARK OFFICE
CERTIFICATE OF CORRECTION

PATENT NO. : 10,468,229 B2
APPLICATION NO. : 15/079403
DATED : November 5, 2019
INVENTOR(S) : Giuseppe Pavia It is certified that error appears in the above-identified patent and that said Letters Patent is hereby corrected as shown below:

In the Specification

Column 15, Line 5, delete "$\alpha^{(47)}$," and insert -- $\varphi^{(47)}$, --;

Column 16, Line 55, delete "FIG." and insert -- FIGS. --;

In the Claims

Column 20, Line 3, Claim 12, delete "according".

Signed and Sealed this
Fifth Day of May, 2020

Andrei Iancu
*Director of the United States Patent and Trademark Office*